US007270821B2

(12) United States Patent
Gehin et al.

(10) Patent No.: US 7,270,821 B2
(45) Date of Patent: Sep. 18, 2007

(54) HEPATITIS B CORE ANTIGEN FUSION PROTEINS

(75) Inventors: Annick Gehin, Leeds (GB); Robert Gilbert, Headington (GB); David Stuart, Headington (GB); David Rowlands, Leeds (GB)

(73) Assignee: University of Leeds Innovations Limited, Leeds (GB)

(*) Notice: Subject to any disclaimer, the term of this patent is extended or adjusted under 35 U.S.C. 154(b) by 143 days.

(21) Appl. No.: 10/240,917

(22) PCT Filed: Apr. 9, 2001

(86) PCT No.: PCT/GB01/01607

§ 371 (c)(1),
(2), (4) Date: Feb. 4, 2003

(87) PCT Pub. No.: WO01/77158

PCT Pub. Date: Oct. 18, 2001

(65) Prior Publication Data

US 2004/0223965 A1 Nov. 11, 2004

(30) Foreign Application Priority Data

Apr. 7, 2000 (EP) ................................. 00107118

(51) Int. Cl.
*A61K 39/00* (2006.01)

(52) U.S. Cl. .................................................. 424/192.1

(58) Field of Classification Search ................ 436/518, 436/819, 820; 530/350, 402, 403, 810; 435/325, 435/344.1; 424/1.11, 1.49, 1.57, 130.1, 133.1, 424/178.9, 192.1

See application file for complete search history.

(56) References Cited

U.S. PATENT DOCUMENTS

| | | | | |
|---|---|---|---|---|
| 5,969,126 A * | 10/1999 | Potter et al. | ............... | 536/23.5 |
| 6,180,343 B1 * | 1/2001 | Anderson et al. | .............. | 435/6 |
| 2003/0021804 A1 * | 1/2003 | Needleman et al. | ..... | 424/193.1 |
| 2004/0054139 A1 * | 3/2004 | Page et al. | .................. | 530/350 |
| 2004/0106174 A1 * | 6/2004 | Jones et al. | ................ | 435/69.1 |
| 2004/0156863 A1 * | 8/2004 | Page et al. | ............... | 424/189.1 |

FOREIGN PATENT DOCUMENTS

| | | |
|---|---|---|
| EP | 0421635 A1 | 4/1991 |
| WO | WO97/35008 | 9/1997 |

OTHER PUBLICATIONS

Kratz et al. Native display of complete foreign protein domains on the surface of hepatitis B virus capsids. Proc. Natl. Acad. Sci. USA, 1999, vol. 96, pp. 1915-1920.*

Schodel et al. The position of heterologous epitopes inserted in hepatitis B virus core particles determines their immunogenicity. Journal of Virology. Jan. 1992, vol. 66, No. 1, p. 106-114.*

Schodel et al. Hybrid hepatitis B virus core antigen as a vaccine carrier moiety: I. Presentation of foreign epitopes. Journal of Biotechnology. 1996, vol. 44, p. 91-96.*

Kratz et al. "Native display of complete foreign protein domains on the surface of hepatitis B virus capsids" Proceedings of the National Academy of Sciences U.S.A., 96:1915-1920 (Mar. 1999).

Ulrich et al., "Core particles of hepatitis B virus as carrier for foreign epitopes" Advances in Virus Research, 50:141-182 (1998).

* cited by examiner

*Primary Examiner*—Bruce R. Campell
*Assistant Examiner*—Emily M. Le
(74) *Attorney, Agent, or Firm*—Nixon & Vanderhye P.C.

(57) ABSTRACT

The hepatitis B virus (HBV) capsid is made up of a single species of protein called the core antigen (HBcAg) which self-assembles into particles. The particles are highly immunogenic and are able to present heterologous epitopes to the immune system when the epitopes are inserted into a surface-exposed region of the particles called the "e1 loop". The structural building blocks of the particles are tightly associated dimers of HBcAg in which the adjacent e1 loops are closely juxtaposed. It is proposed that sequences inserted into the e1 loop are conformationally restrained in the assembled particles when presented in monomeric core protein. The invention seeks to solve this problem by covalently linking core proteins as tandem copies (e.g., as dimers) so that insertions can be made independently in each copy. This is particularly useful for insertion of large sequences into the e1 loop because it allows such sequences to be inserted into just one copy of the core protein per tandem repeat, thereby reducing potential conformational clashes in assembly. Alternatively, a different sequence may be inserted into each e1 loop of a tandem repeat, thus increasing the flexibility of HBcAg particles as an epitope delivery system.

36 Claims, 4 Drawing Sheets

SEQUENCE LISTING

```
<160> NUMBER OF SEQ ID NOS: 11

<210> SEQ ID NO 1
<211> LENGTH: 639
<212> TYPE: DNA
<213> ORGANISM: Hepatitis B virus
<220> FEATURE:
<221> NAME/KEY: CDS
<222> LOCATION: (1)..(639)

<400> SEQUENCE: 1

atg caa ctt ttt cac ctc tgc cta atc atc tct tgt tca tgt cct act        48
Met Gln Leu Phe His Leu Cys Leu Ile Ile Ser Cys Ser Cys Pro Thr
  1               5                  10                  15

gtt caa gcc tcc aag ctg tgc ctt ggg tgg ctt tgg ggc atg gac atc        96
Val Gln Ala Ser Lys Leu Cys Leu Gly Trp Leu Trp Gly Met Asp Ile
             20                  25                  30

gac cct tat aaa gaa ttt gga gct act gtg gag tta ctc tcg ttt ttg       144
Asp Pro Tyr Lys Glu Phe Gly Ala Thr Val Glu Leu Leu Ser Phe Leu
         35                  40                  45

cct tct gac ttc ttt cct tca gta cga gat ctt cta gat acc gcc tca       192
Pro Ser Asp Phe Phe Pro Ser Val Arg Asp Leu Leu Asp Thr Ala Ser
     50                  55                  60

gct ctg tat cgg gaa gcc tta gag tct cct gag cat tgt tca cct cac       240
Ala Leu Tyr Arg Glu Ala Leu Glu Ser Pro Glu His Cys Ser Pro His
 65                  70                  75                  80

cat act gca ctc agg caa gca att ctt tgc tgg ggg gaa cta atg act       288
His Thr Ala Leu Arg Gln Ala Ile Leu Cys Trp Gly Glu Leu Met Thr
                 85                  90                  95

cta gct acc tgg gtg ggt gtt aat ttg gaa gat cca gcg tct aga gac       336
Leu Ala Thr Trp Val Gly Val Asn Leu Glu Asp Pro Ala Ser Arg Asp
            100                 105                 110

cta gta gtc agt tat gtc aac act aat atg ggc cta aag ttc agg caa       384
Leu Val Val Ser Tyr Val Asn Thr Asn Met Gly Leu Lys Phe Arg Gln
        115                 120                 125

ctc ttg tgg ttt cac att tct tgt ctc act ttt gga aga gaa aca gtt       432
Leu Leu Trp Phe His Ile Ser Cys Leu Thr Phe Gly Arg Glu Thr Val
    130                 135                 140

ata gag tat ttg gtg tct ttc gga gtg tgg att cgc act cct cca gct       480
Ile Glu Tyr Leu Val Ser Phe Gly Val Trp Ile Arg Thr Pro Pro Ala
145                 150                 155                 160

tat aga cca cca aat gcc cct atc cta tca aca ctt ccg gag act act       528
Tyr Arg Pro Pro Asn Ala Pro Ile Leu Ser Thr Leu Pro Glu Thr Thr
                165                 170                 175

gtt gtt aga cga cga ggc agg tcc cct aga aga aga act ccc tcg cct       576
Val Val Arg Arg Arg Gly Arg Ser Pro Arg Arg Arg Thr Pro Ser Pro
            180                 185                 190

cgc aga cga agg tct caa tcg ccg cgt cgc aga aga tct caa tct cgg       624
Arg Arg Arg Arg Ser Gln Ser Pro Arg Arg Arg Arg Ser Gln Ser Arg
        195                 200                 205

gaa tct caa tgt tag                                                   639
Glu Ser Gln Cys
    210

<210> SEQ ID NO 2
```

-continued

<211> LENGTH: 212
<212> TYPE: PRT
<213> ORGANISM: Hepatitis B virus

<400> SEQUENCE: 2

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Glu Leu Met Thr
85 90 95

Leu Ala Thr Trp Val Gly Val Asn Leu Glu Asp Pro Ala Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro
180 185 190

Arg Arg Arg Arg Ser Gln Ser Pro Arg Arg Arg Arg Ser Gln Ser Arg
195 200 205

Glu Ser Gln Cys
210

<210> SEQ ID NO 3
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 3
gttaccatgg acattgaccc ttat 24

<210> SEQ ID NO 4
<211> LENGTH: 72
<212> TYPE: DNA
<213> ORGANISM: Artificial Sequence
<220> FEATURE:
<223> OTHER INFORMATION: oligonucleotide primer

<400> SEQUENCE: 4
gtccatagaa ccaccagaac caccagaacc accagaacca ccagaaccac cagaaacaac 60
agtagtttcc gg 72

<210> SEQ ID NO 5
<211> LENGTH: 81
<212> TYPE: DNA
<213> ORGANISM: Artificial Sequence -continued

```
<220> FEATURE:
<223> OTHER INFORMATION: oligonucleotide primer

<400> SEQUENCE: 5

gtccatagaa ccaccagaac caccagaacc accagaacca ccagaaccac cagaaccacc     60

agaaacaaca gtagtttccg g                                               81


<210> SEQ ID NO 6
<211> LENGTH: 90
<212> TYPE: DNA
<213> ORGANISM: Artificial Sequence
<220> FEATURE:
<223> OTHER INFORMATION: oligonucleotide primer

<400> SEQUENCE: 6

gtccatagaa ccaccagaac caccagaacc accagaacca ccagaaccac cagaaccacc     60

agaaccacca gaaacaacag tagtttccgg                                      90


<210> SEQ ID NO 7
<211> LENGTH: 69
<212> TYPE: DNA
<213> ORGANISM: Artificial Sequence
<220> FEATURE:
<223> OTHER INFORMATION: oligonucleotide primer

<400> SEQUENCE: 7

gttgttggtg gttctggtgg ttctggtggt tctggtggtt ctggtggttc tatggacatt     60

gacccttat                                                             69


<210> SEQ ID NO 8
<211> LENGTH: 78
<212> TYPE: DNA
<213> ORGANISM: Artificial Sequence
<220> FEATURE:
<223> OTHER INFORMATION: oligonucleotide primer

<400> SEQUENCE: 8

gttgttggtg gttctggtgg ttctggtggt tctggtggtt ctggtggttc tggtggttct     60

atggacattg acccttat                                                   78


<210> SEQ ID NO 9
<211> LENGTH: 87
<212> TYPE: DNA
<213> ORGANISM: Artificial Sequence
<220> FEATURE:
<223> OTHER INFORMATION: oligonucleotide primer

<400> SEQUENCE: 9

gttgttggtg gttctggtgg ttctggtggt tctggtggtt ctggtggttc tggtggttct     60

ggtggttcta tggacattga cccttat                                         87


<210> SEQ ID NO 10
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 10

tatgaagctt atgagtccaa gga                                             23


<210> SEQ ID NO 11
```

-continued

```
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 11

tatgaagctt ccgtcgtcaa acaa                                    24
```

HEPATITIS B CORE ANTIGEN FUSION PROTEINS

This application is a U.S. national phase of international application No. PCT/GB01/01607 filed 9 Apr. 2001, which designated the U.S. and was published in English.

The invention relates to hepatitis B core antigen fusion proteins, particles containing the proteins, nucleic acid molecules encoding the proteins, processes for producing the proteins, pharmaceutical compositions containing the proteins and use of the proteins in prophylactic and therapeutic vaccination.

BACKGROUND TO THE INVENTION

Hepatitis B is a major healthcare problem throughout both the developed and developing world. Infection with the hepatitis B virus (HBV) can result in an acute or chronic disease which in a proportion of cases may lead to hepatocellular carcinoma and death. The virus is double shelled, and its DNA is protected inside a protein structure called the core antigen (HBcAg). The core is surrounded by the envelope protein known as the surface or S antigen (HBsAg). HBcAg is an unusual antigen which can be used as a delivery vehicle for specific peptides to the immune system. The antigen has been used to present T-helper, B and cytotoxic lymphocyte (CTL) epitopes from a variety of viral and bacterial pathogens, including epitopes from the surface antigen of HBV, envelope proteins from hepatitis A virus and antigens from hepatitis C virus. For a review see Ulrich et al (1998) Advances in Virus Research 50 141-182.

HBcAg is an excellent vehicle for the presentation of epitopes due to the molecular structure of the protein, which self-assembles into particles. Each particle is generated from either 180 or 240 copies of a monomeric polypeptide. The monomer, on reaching an appropriate concentration inside the host cell, forms a particle of approximately 27 nm in diameter. Structural studies have shown that amino acids within the region from residues 68 to 90 form a spiked structure on the surface of the particle which is known as the e1 loop. Two monomers joined by disulphide bonds link to form a dimer spike, the most exposed amino acid being at position 80 (at the centre of the e1 loop).

EP-A421635 (The Wellcome Foundation Limited) describes modification of the HBV core gene to allow insertion of foreign epitopes into the e1 loop without altering the potential of the protein to from particles. Insertion at this site allows maximum exposure of the inserted epitope on the tip of each spike created by dimers of the protein. As there are approximately 180 or 240 copies of each monomer per particle, each particle is able to present 180 or 240 copies of the epitope of interest

SUMMARY OF THE INVENTION

In the dimers of HBcAg which form the structural building blocks of core particles, adjacent e1 loops are closely juxtaposed. It is proposed that sequences inserted into the e1 loop are conformationally restrained in the assembled particles when presented in monomeric core protein. The invention seeks to solve this problem by covalently linking core proteins as tandem copies, e.g. as dimers, so that insertions can be made independently in each copy. This is particularly useful for insertion of large sequences into the e1 loop because it allows such sequences to be inserted into just one copy of the core protein per tandem repeat, thereby reducing potential conformational clashes in assembly. Alternatively, a different sequence may be inserted into each e1 loop of a tandem repeat, thus increasing the flexibility of HBcAg particles as an epitope presentation system.

Thus, the invention provides a protein comprising tandem copies of HBcAg. The protein is generally a dimer comprising two copies of HBcAg. A heterologous epitope may be inserted into the e1 loop of one or more of the copies of HBcAg. The protein assembles into particles which present the heterologous epitope inserted in the e1 loop on their surfaces and are useful in the prophylactic and therapeutic vaccination of humans and animals.

DETAILED DESCRIPTION OF THE INVENTION

The Protein

The basic building block of the protein of the invention is HBcAg, which has 183 or 185 amino acids (aa) depending on the subtype of HBV. The sequence of the 183 amino acid protein of the ayw subtype plus a 29 amino acid pre-sequence is shown in SEQ ID No. 2. The mature HBcAg runs from the Met residue at position 30 to the Cys residue at the extreme C-terminus, with the sequence from positions 1 to 29 being a pre-sequence.

The protein generally comprises only two copies of HBcAg forming a dimer because dimers of HBcAg form the structural building blocks of core particles. However, the protein may comprise further copies of HBcAg. Thus, the protein may comprise from 2 to 8 copies or from 2 to 4 copies of HBcAg. The use of more than two copies increases the flexibility of the system; for example, the use of three copies allows three different epitopes to be inserted into three e1 loops in the protein of the invention and thereby increases the breadth of the immune response induced by the protein of the invention.

The HBcAg units are generally joined together in a head-to-toe fashion, i.e. the C-terminus of one unit is joined to the N-terminus of the adjacent unit. The units may be joined directly by a covalent bond (e.g. a peptide bond), but preferably they are joined by a linker which spaces the adjacent units apart and thereby prevents any problem with disruption of the packing of adjacent units. The nature of the linker is discussed below.

One or more of the HBcAg units in the protein of the invention may be native full length HBcAg. However, generally at least one of the units is a modified form of HBcAg, for example HBcAg modified by insertion of a heterologous epitope in the e1 loop. In dimers according to the invention, one of the HBcAg units may be modified and the other may be native HBcAg.

As a general rule, any modifications are chosen so as not to interfere with the conformation of HBcAg and its ability to assemble into particles. Such modifications are made at sites in the protein which are not important for maintenance of its conformation, for example in the e1 loop, the C-terminus and/or the N-terminus. The e1 loop of HBcAg can tolerate insertions of e.g. from 1 to 120 amino acids without destroying the particle-forming ability of the protein.

The HBcAg sequence may be modified by a substitution, insertion, deletion or extension. The size of insertion, deletion or extension may, for example, be from 1 to 200 aa, from 3 to 100 aa or from 6 to 50 aa. Substitutions may involve a number of amino acids up to, for example, 1, 2, 5, 10, 20 or 50 amino acids over the length of the HBcAg sequence. An extension may be at the N- or C-terminus of HBcAg. A deletion may be at the N-terminus, C-terminus or at an internal site of the protein. Substitutions may be made at any position in the protein sequence. Insertions may also be made at any point in the protein sequence, but are typically made in surface-exposed regions of the protein such as the e1 loop. An inserted sequence may carry a heterologous epitope. More than one modification may be made to each HBcAg unit. Thus, it is possible to make a terminal extension or deletion and also an internal insertion. For example, a truncation may be made it the C-terminus and an insertion may be made in the e1 loop.

Substitutions will generally be conservative and may be made, for example, according to the following Table, in which amino acids in the same block in the second column and preferably in the same line in the third column may be substituted for each other.

| | | |
|---|---|---|
| ALIPAHTIC | Non-polar | G A P |
| | Polar-uncharged | C S T M |
| | | NQ |
| | Polar-charged | D E |
| | | K R |
| AROMATIC | | H F W Y |

Each part of the HBcAg sequence in the protein of the invention preferably has at least 70% sequence identity to the corresponding sequence of a natural HBcAg protein, such as the protein having the sequence shown in SEQ ID NO: 2. More preferably, the identity is at least 80%, at least 90%, at least 98%, at least 97% or at least 99%. Methods of measuring protein sequence (and nucleic acid sequence) identity are well known in the art. For example, the UWGCG Package provides the BESTFIT programme (Devereux et al (1984) *Nucleic Acids Research* 12, p. 387-395). Similarly, the PILEUP and BLAST algorithms can be used to line up sequences (for example as described in Altschul S. F. (1993) *J. Mol. Evol.* 36:290-300 and Altschul, S. F. et al (1990) *J. Mol. Biol.* 215:403-10).

The e1 loop of HBcAg is at positions 68 to 90, and a heterologous epitope may be inserted anywhere between these positions. Preferably, the epitope is inserted in the region from positions 69 to 90, 71 to 90 or 75 to 85. Most preferred is to insert the epitope between amino acid residues 79 and 80 or between residues 80 and 81. When a heterologous epitope is inserted, the entire sequence of HBcAg may be maintained, or alternatively the whole or a part of the e1 loop sequence may be deleted and replaced by the heterologous sequence. Thus, amino acid residues 69 to 90, 71 to 90 or 75 to 85 may be replaced by a heterologous epitope. Where a heterologous epitope replaces e1 loop sequence, the epitope is generally not shorter than the sequence that it replaces.

A C-terminal truncation of HBcAg will generally not go beyond aa 144 because if any further truncation is made particles may not form. Thus, the deleted amino acids may, for example, comprise aa 144 to the C-terminal aa (aa 183 or 185), aa 150 to the C-terminal aa, aa 164 to the C-terminal aa or aa 172 to the C-terminal aa. The C-terminus of HBcAg binds DNA, and truncation of the C-terminus therefore reduces or completely removes DNA from preparations of HBcAg and HBcAg hybrid proteins.

The protein of the invention forms particles which preferably resemble the particles formed by native HBcAg. The particles of the invention are typically at least 10 nm in diameter, for example from 10 to 50 nm or from 20 to 40 n=in diameter, but preferably they are about 27 nm in diameter (which is the size of native HBcAg particles). They comprise multiple HBcAg units, for example from 150 to 300 units, but generally they are fixed to about 180 or about 240 units (which are the numbers of units in native HBcAg particles). Where the protein of the invention is a dimer, this means that the number of protein monomers in the particles may be from 75 to 150 but is generally about 90 or about 120.

The linker between adjacent HBcAg units is generally a chain of amino acids at least 1.5 nm (15 Å) in length, for example from 1.5 to 10 nm, from 1.5 to 5 nm or from 1.5 to 3 nm. It may, for example, comprise 4 to 40 aa or 10 to 30 aa, preferably 15 to 21 aa. The linker is generally flexible. The amino acids in the linker may, for example, include or be entirely composed of glycine, serine and/or proline. A preferred linker comprises one or more repeats of the sequence GlyGlySer (GGS). Alternatively, the linker may comprise one or more GlyPro (GP) dipeptide repeats. The number of repeats may, for example, be from 1 to 18, preferably from 3 to 12. In the case of GGS repeats, the use of 5, 6 or 7 repeats has been found to allow the formation of particles. The linker may correspond to the hinge region of an antibody; this hinge region is thought to provide a flexible joint between the antigen-binding and tail domains of antibodies.

As indicated above, a heterologous epitope may be inserted into one or more of the copies of HBcAg in the protein of the invention, preferably into the e1 loop. A "heterologous" epitope is an epitope that is not normally located at the position at which it is located in the HBcAg; it is generally from a protein other than HBcAg but it may be from a different location in HBcAg. The epitope comprises a sequence of amino acids which raises an immune response. The epitope may be conformational or linear. It may be, for example, in a sequence of from 6 to 120 aa, from 6 to 50 aa or from 6 to 20 aa. A major advantage of the invention is that it allows epitopes carried on large sequences to be inserted into the e1 loop, for example on sequences of from 30 to 120 aa, 40 to 120 aa or 60 to 120 aa.

The protein of the invention may contain more than one heterologous epitope, for example up to 2, 3, 5 or 8 heterologous epitopes, and in this case the epitopes may be present in the same or different HBcAg units. More than one copy of an epitope may be inserted in each HBcAg unit; for example, from 2 to 8 copies may be inserted. Where there are two or more heterologous epitopes in the protein of the invention, they may be from the same or different organisms and from the same or different proteins.

The epitope may be a T-cell or a B-cell epitope. If it is a T-cell epitope, it may be a cytotoxic T-lymphocyte (CTL) epitope or a T-helper (Th) cell epitope (e.g. a Th1 or Th2 epitope). In a preferred embodiment of the invention, one of the epitopes is a T-helper cell epitope and another is a B-cell or a CTL epitope. The presence of the T-helper cell epitope enhances the immune response against the B-cell or CTL epitope.

The choice of epitope depends on the disease that it is wished to vaccinate against. The epitope may, for example, be from a pathogenic organism, a cancer-associated antigen or an allergen. The pathogenic organism may, for example, be a virus, a bacterium or a protozoan.

Examples of pathogens whose epitopes may be inserted include hepatitis A virus (HAV), HBV, HCV, influenza virus, foot-and-mouth disease virus, poliovirus, herpes simplex virus, rabies virus, feline leukemia virus, human immunodeficiency virus type 1 (HIV1), human immunodeficiency virus type 2 (HIV2), simian immunodeficiency virus (SIV), human rhinovirus, dengue virus, yellow fever virus, human papilloma virus, respiratory syncytial virus, *Plasmodium falciparum* (a cause of malaria), and bacteria such as *Mycobacteria, Bordetella, Salmonella, Escherichia, Vibrio, Haemophilus, Neisseria, Yersinia* and *Brucella*. Specifically, the bacterium may be *Mycobacterium tuberculosis*—the cause of tuberculosis; *Bordetella pertussis* or *Bordetella parapertussis*—causes of whooping cough; *Salmonella typhimurium*—the cause of salmonellosis in several animal species; *Salmonella typhi*—the cause of human typhoid; *Salmonella enteritidis*—a cause of food poisoning in humans; *Salmonella choleraesuis*—a cause of salmonellosis in pigs; *Salmonella dublin*—a cause of both a systemic and diarrhoeal disease in cattle, especially in new-born calves; *Escherichia coli*—a cause of food poisoning in humans; *Haemophilus influenzae*—a cause of meningitis; *Neisseria gonorrhoeae*—a cause of gonnorrhoeae; *Yersinia enterocolitica*—the cause of a spectrum of diseases in humans ranging from gastroenteritis to fatal septicemic disease; and *Brucella abortus*—a cause of abortion and infertility in cattle and a condition known as undulant fever in humans.

Examples of candidate epitopes for use in the invention include epitopes from the following antigens: the HIV antigens gp 120, gp 160, gag, pol, Nef, Tat and Ref; the malaria antigens CS protein and Sporozoite surface protein 2; the influenza antigens HA, NP and NA; the herpes virus antigens EBV gp340, EBV gp85, HSV gB, HSV gD, HSV gH, HSV early protein product, cytomegalovirus gB, cytomegalovirus gH, and IE protein gP72; the human papilloma virus antigens E4, E6 and E7; the respiratory syncytial virus antigens F protein, G protein, and N protein; the pertactin antigen of *B. pertussis*; the tumor antigens carcinoma CEA, carcinoma associated mucin, carcinoma P53, melanoma MPG, melanoma P97, MAGE antigen, carcinoma Neu oncogene product, prostate specific antigen (PSA), prostate associated antigen, ras protein, and myc; and house dust mite allergen.

Especially preferred epitopes are those from the pre-S1 region, the pre-S2 region, the S region or core antigen of HBV. It is possible to insert the whole of the pre-S1 and/or the whole of the pre-S2 region into HBcAg, but generally only a part of one of the regions is inserted. The inserted part is typically at least 6 amino acids in length, for example from 6 to 120 aa, 20 to 80 aa or 20 to 50 aa. The insert may include, for example, the residues at pre-S1 positions 1-9, 10-19, 20-29, 30-39, 40-49, 50-59, 60-69, 70-79, 80-89, 90-99, 100-109 or 110-119 or the residues at pre-S2 positions 120-129, 130-139, 140-149, 150-159, 160-169 or 170-174. Particularly preferred inserts are pre-S1 residues 20-47 and pre-S2 residues 139-174.

Making the Proteins of the Invention

The proteins of the invention are generally made by recombinant DNA technology. The invention includes a nucleic acid molecule (e.g. DNA or RNA) encoding a protein of the invention, such as an expression vector. The nucleic acid molecules may be made using known techniques for manipulating nucleic acids. Typically, two separate DNA constructs encoding two HBcAg units are made and then joined together by overlapping PCR.

A protein of the invention may be produced by culturing a host cell containing a nucleic molecule encoding the protein under conditions in which the protein is expressed, and recovering the protein. Suitable host cells include bacteria such as *E. coli*, yeast, mammalian cells and other eukaryotic cells, for example insect Sf9 cells.

The vectors constituting nucleic acid molecules according to the invention may be, for example, plasmid or virus vectors. They may contain an origin of replication, a promoter for the expression of the sequence encoding the protein, a regulator of the promoter such as an enhancer, a transcription stop signal, a translation start signal and/or a translation stop signal. The vectors may also contain one or more selectable marker genes, for example an ampicillin resistance gene in the case of a bacterial plasmid or a neomycin resistance gene in the case of a mammalian vector. Vectors may be used in vitro, for example for the production of RNA or used to transform or transfect a host cell. The vector may also be adapted to be used in vivo, for example in a method of gene therapy or DNA vaccination.

Promoters, enhancers and other expression regulation signals may be selected to be compatible with the host cell for which the expression vector is designed. For example, prokaryotic promoters maybe used, in particular those suitable for use in *E. coli* strains (such as *E. coli* HB101). A promoter whose activity is induced in response to a change in the surrounding environment, such as anaerobic conditions, may be used. Preferably an htrA or nirB promoter may be used. These promoters may be used in particular to express the protein in an attenuated bacterium, for example for use as a vaccine. When expression of the protein of the invention is carried out in mammalian cells, either in vitro or in vivo, mammalian promoters may be used. Tissue-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters and adenovirus promoters. All these promoters are readily available in the art.

A protein according to the invention maybe purified using conventional techniques for purifying proteins. The protein may, for example, be provided in purified, pure or isolated form. For use in a vaccine, the protein must generally be provided at a high level of purity, for example at a level at which it constitutes more than. 80%, more than 90%, more than 95% or more than 98% of the protein in the preparation. However, it may be desirable to mix the protein with other proteins in the final vaccine formulation.

Vaccination Against Diseases

The primary use of the proteins of the invention is as therapeutic or prophylactic vaccines. The invention includes a pharmaceutical composition (e.g. a vaccine composition) comprising a protein of the invention, a particle of the invention or a nucleic acid molecule of the invention and a pharmaceutically acceptable carrier or diluent.

The principle behind prophylactic vaccination is to induce an immune response in a host so as to generate an immunological memory in the host. This means that, when the host is exposed to the virulent pathogen, it mounts an effective (protective) immune response, i.e. an immune response which inactivates and/or kills the pathogen. The invention could form the basis of a prophylactic vaccine against a range of diseases and conditions, such as HBV, HAV, HCV, influenza, foot-and-mouth disease, polio, herpes, rabies, AIDS, dengue fever, yellow fever, malaria, tuberculosis, whooping cough, typhoid, food poisening, diarrhoea, meningitis and gonorrhoea. The epitopes in the protein of the invention are chosen so as to be appropriate for the disease against which the vaccine is intended to provide protection.

The principle behind therapeutic vaccination is to stimulate the immune system of the host to alleviate or eradicate a disease or condition. There are a number of diseases and conditions which may be susceptible to therapeutic vaccination, such as chronic viral diseases including chronic HBV and chronic HCV, cancer, and allergies such as asthma, atopy, eczema, rhinitis and food allergies.

Chronic viral diseases arise when the immune system of an infected host fails to eliminate the virus, allowing the virus to persist in the host for a long period of time. The invention may be used to induce the immune system of the chronically infected individual so as to eliminate the virus. For example, is believed that patients with chronic hepatitis have an inadequate T-cell response, and that stimulation of an appropriate T-cell response can eliminate the virus. Thus, in order to treat chronic viral hepatitis using the invention, T-cell epitopes may be inserted into the protein of the invention, such as T-cell epitopes from the pre-S1 and pre-S2 regions of HBV.

Similarly, in the case of cancer, it is believed that enhancement of the T-cell response to tumour antigens may help the immune system to destroy the tumour. It is believed that allergic diseases are caused at least in part by an unbalanced T-cell response in which an inflammatory Th2 responses dominates over an antagonistic Th1 response, and that allergies may therefore be treated by enhancing the Th1 response. This can be achieved according to the invention by using a protein containing a heterologous epitope which stimulates a Th1 response.

Suitable carriers and diluents for inclusion in pharmaceutical compositions of the invention are isotonic saline solutions, for example phosphate-buffered saline. The composition will normally include an adjuvant, such as aluminium hydroxide. The composition may be formulated in liquid form for injection. The composition comprises the protein, particles or nucleic acid in a prophylactically or therapeutically effective amount. Typically, the protein or particles are administered in a dose of from 0.1 to 200 μg, preferably from 1 to 100 μg, more preferably from 10 to 50 μg body weight. The nucleic acid of the invention may be administered directly as a naked nucleic acid construct using techniques known in the art or using vectors known in the art. The amount of nucleic acid administered is typically in the range of from 1 μg to 10 mg, preferably from 100 μg to 1 mg. The vaccine may be given in a single dose schedule or a multiple dose schedule, for example in from 2 to 32 or from 4 to 16 doses. The routes of administration and doses given above are intended only as a guide, and the route and dose may ultimately be at the discretion of the physician.

Experimental Section

BRIEF DESCRIPTION OF THE DRAWINGS

FIG. 6(*a*) shows tandem core particle (the left-hand particle) in comparison with a native particle (the middle particle). The right-hand part of FIG. 6(*a*) shows the C-terminal part of core antigen in a tandem core particle. FIG. 6(*b*) shows the fitting of a portion of the structure of a tandem core particle with a native particle.

Methods

Figure 1:
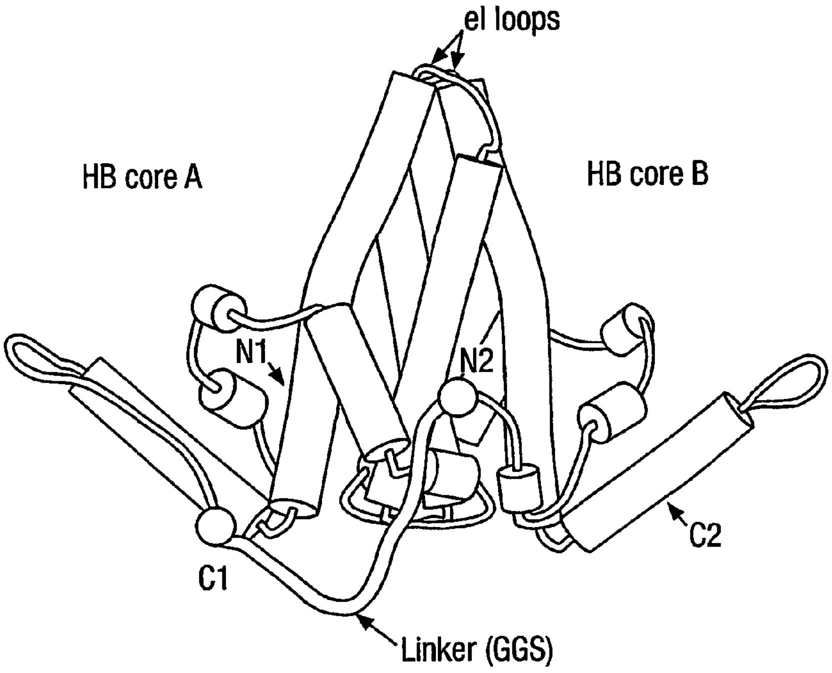
FIG. 1: A hypothetical model showing the feasibility of a linked AB dimer of hepatitis B core.
Figure 2:
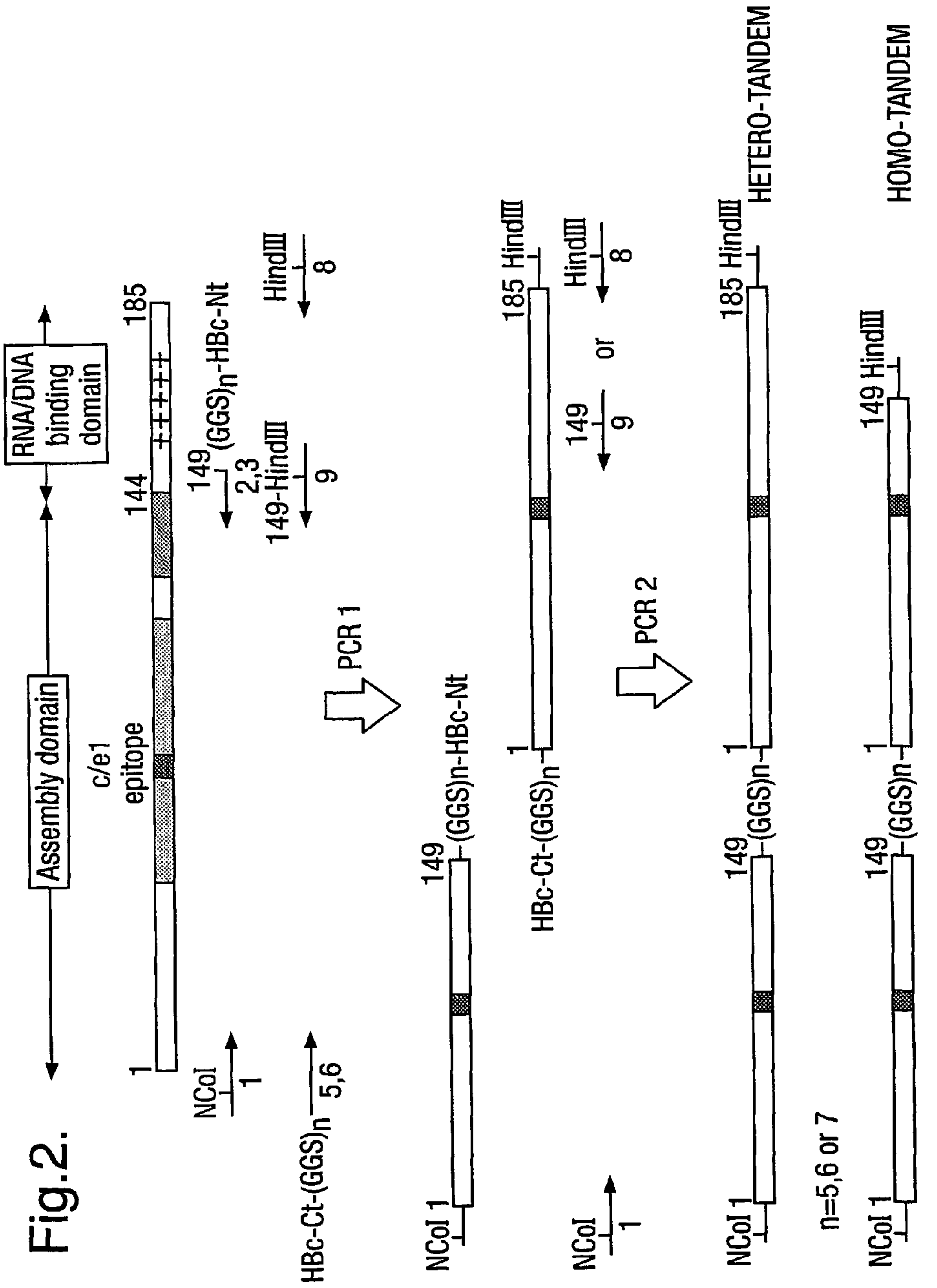
FIG. 2: A schematic representation of the construction of hetero- and homo-tandem cores. The bars represent the primary structures of the proteins. Within the assembly domain of HBcAg (amino acids 1-144), the e1 loop (black rectangle) and the regions involved in intradimer (light shading) and interdimer (dark shading) contacts are indicated. The Arg-rich nucleic acid binding domain is symbolised by +. Primers (Table 1) are indicated as arrows.

Examination of the HBV core particle structure suggested that a flexible linker of at least 1.5 nm (15 Å) could be used to link the two proteins in a dimer pair without disrupting their structural integrity (FIG. 1). Consequently, constructs were made by overlapping PCRs in which the upstream core protein was truncated to residue 149 and then linked to a downstream copy via 5, 6 or 7 copies of a GlyGlySer (GGS) repeat sequence (FIG. 2).

The downstream copy was either the full length core protein or was truncated at amino acid 149 to remove the Arg-rich C-terminal region. Table 1 gives the oligonucleotide sequences used to construct the various HBV tandem cores.

The constructs were cloned into ptrc99A expression vector, transformed into *E. coli* JM 109 and induced with IPTG. Cells were then harvested by centrifugation, resuspended into PBS and sonicated twice. Lysates containing soluble expressed tandem cores were made 30% saturated ammonium sulphate and the precipitated proteins collected by centrifugation, resuspended into PBS and dialysed against phosphate-buffered saline. The clarified lysate was loaded onto 15-45% linear sucrose gradients and centrifuged at 28,000 rpm for 4 hours at 4° C. Gradients were fractionated from the bottom of the tube into 2 ml aliquots and analysed by SDS-PAGE and Western Blotting using a monoclonal primary antibody against HBV core protein (mAb 13).

HBV core particle preparations were spotted onto carbon coated grids, negatively stained with uracyl acetate and visualized in transmission electron microscopy. The structures of the core particles were determined using cryo-electronmicroscopy.

TABLE 1

Sequences of the oligonucleotide primers (SEQ ID NOS:3-11, respectively) used for cloning HBV tandem core genes into ptrc99A.

| Primers | Sequences (5'→3') |
|---|---|
| 1 | G**TTACCATG**GACATTGACCCTTAT[a] |
| 2 | GTCCATAGA(ACCACCAGA)$_5$AACAACAGTAGTTTCCGG |
| 3 | GTCCATAGA(ACCACCAGA)$_6$AACAACAGTAGTTTCCGG |
| 4 | GTCCATAGA(ACCACCAGA)$_7$AACAACAGTAGTTTCCGG |
| 5 | GTTGTT(GGTGGTTCT)$_5$ATGGACATTGACCCTTAT |
| 6 | GTTGTT(GGTGGTTCT)$_6$ATGGACATTGACCCTTAT |
| 7 | GTTGTT(GGTGGTTCT)$_7$ATGGACATTGACCCTTAT |
| 8 | TATG**AAGCTT**ATGAGTCCAAGGA[b] |
| 9 | TATG**AAGCTT**CCGTCGTCAAACAA[b] |

[a]NcoI restriction site is boldfaced
[b]HindIII restriction site is boldfaced

Results

Figure 3:
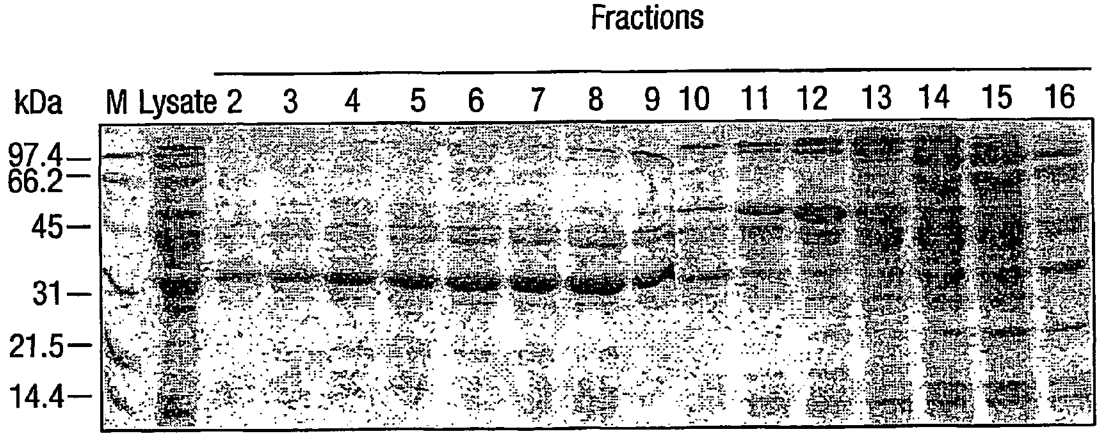
FIG. 3: A 12% SDS-PAGE of fractions from a sucrose density gradient separation of homo-tandem core particles.
Figure 4:
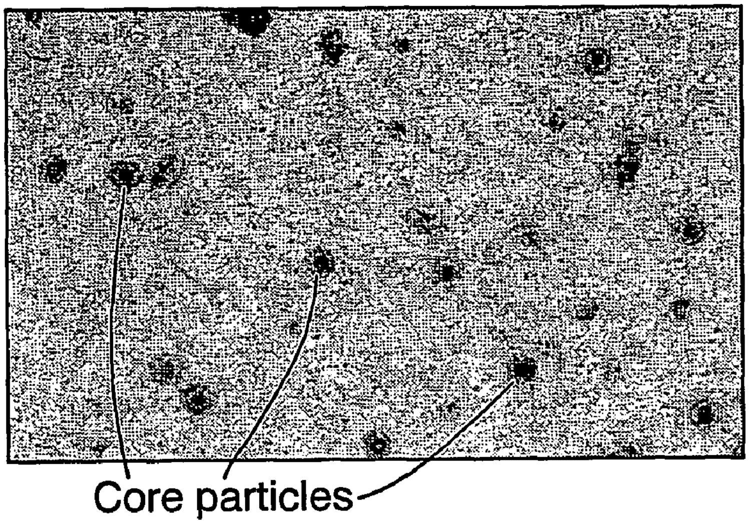
FIG. 4: Electron micrograph of hetero-tandem core particles with a linker comprising five repeats of GGS.
Figure 5:
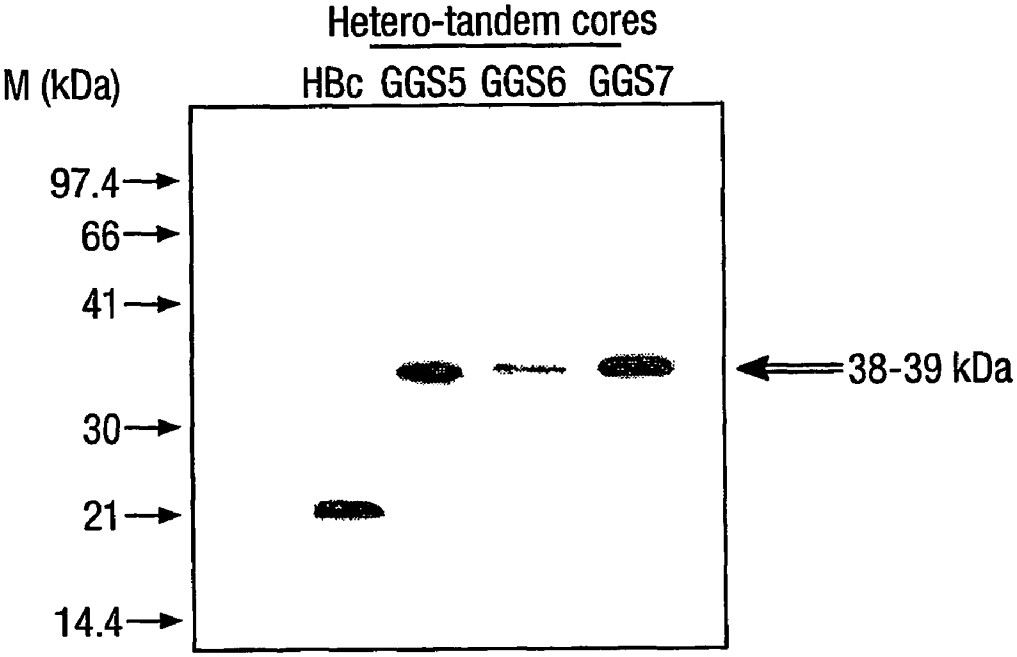
FIG. 5: A Western blot showing the efficient expression of hetero-tandem cores in *E. coli*. The cores contained 5, 6 and 7 GGS repeats as the linker respectively (GGS5, GGS6 and GGS7).
Figure 6A:
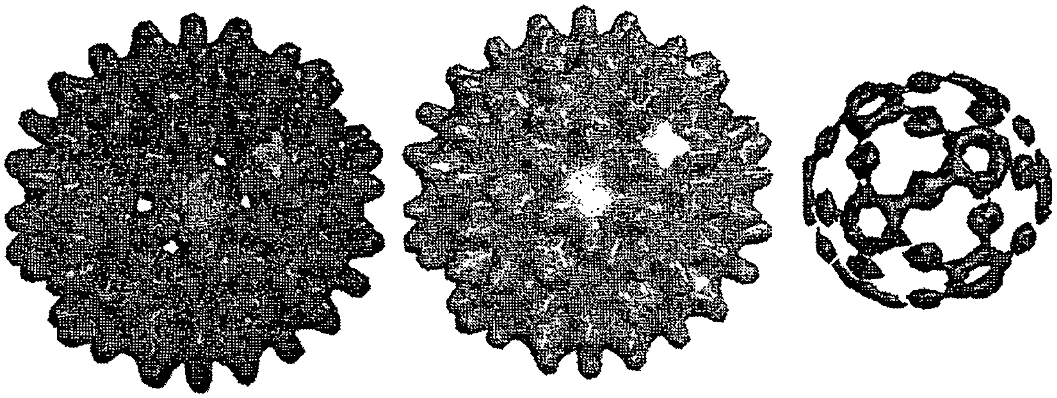
FIG. 6: The results of cryo-electronmicroscopy of tandem core particles.
Figure 6B:
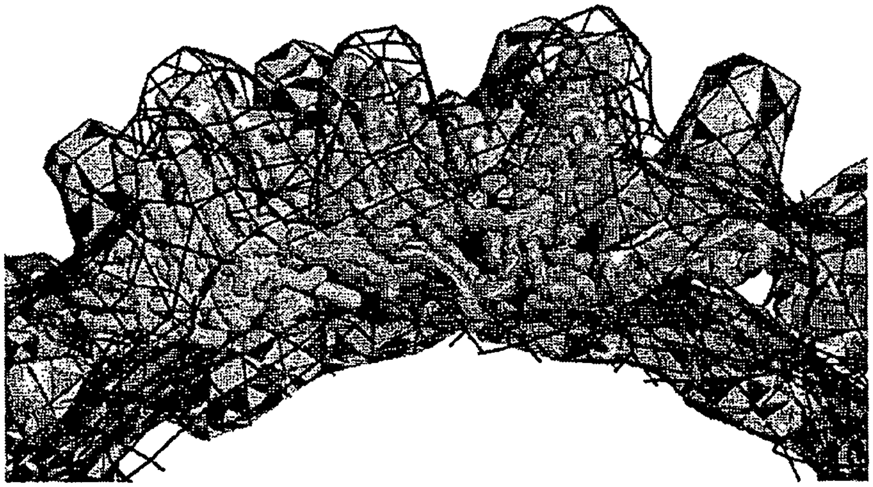

Tandem HBV core proteins with 5, 6 or 7 copies of GGS were all expressed successfully and were shown to migrate in polyacrylamide gels with the expected mobilities. Each assembled into core particles as evidenced by their sedimentation in sucrose density gradients (FIG. 3) and their appearance in the electron microscope (FIG. 4). The particles retained their antigenic properties as demonstrated by their reactivity in ELISA and Western blots (FIG. 5). Furthermore, the structures of the particles formed by the tandem core proteins were indistinguishable from the structure of native core particles in cryo-electronmicroscopy (FIG. 6).

The invention claimed is:

1. An isolated fusion protein comprising a first recombinant hepatitis B core antigen (HBcAg) linked tandemly to a second recombinant HBcAg wherein (a) said first HBcAg and second HBcAg are joined directly or separated by an amino acid linker sequence, (b) one or both of said first HBcAg and said second HBcAg have a heterologous epitope in the e1 loop, (c) the tandemly linked said first HBcAg and second HBcAg form core particles, and (d) one or both of said first HBcAg and said second HBcAg are optionally truncated at the C-terminus with a truncation that does not go beyond amino acid residue 144.

2. The protein according to claim 1 which is a dimer of two copies of HBcAg.

3. The protein according to claim 2 wherein one of said first HBcAg and said second HBcAg has a heterologous epitope in the e1 loop.

4. The protein according to claim 2 wherein both of said first HBcAg and said second HBcAg have a heterologous epitope in the e1 loop.

5. The protein according to claim 4 wherein both of said first HBcAg and said second HBcAg have the same heterologous epitope in the e1 loop.

6. The protein according to claim 4 wherein each of said first HBcAg and said second HBcAg has a different heterologous epitope in the e1 loop.

7. The protein according to claim 2 wherein one or both of the heterologous epitopes are from the pre-S1 or pre-S2 region of hepatitis B virus (HBV).

8. The protein according to claim 2 wherein one or both of the heterologous epitopes consist of an amino acid sequence that is 10 to 120 amino acids residues in length.

9. The protein according to claim 2 wherein one or both of said first HBcAg and said second HBcAg are truncated at the C-terminus.

10. The protein according to claim 2 wherein said first HBcAg and said second HBcAg are joined by a linker.

11. The protein according to claim 10 wherein the linker is at least 1.5 nm in length.

12. The protein according to claim 10 wherein the linker comprises multiple copies of the sequence GlyGlySer (GGS).

13. The protein according to claim 12 wherein the linker comprises 5, 6 or 7 copies of the sequence GGS.

14. An isolated nucleic acid molecule encoding a protein as claimed in claim 1.

15. The nucleic acid molecule according to claim 14 which is an expression vector.

16. An isolated host cell comprising a nucleic acid molecule as claimed in claim 15.

17. A process for producing a protein as claimed in claim 1, which process comprises culturing an isolated host cell containing a nucleic acid molecule which encodes the protein under conditions in which the protein is expressed, and recovering the protein.

18. A particle comprising multiple copies of an isolated fusion protein comprising a first recombinant hepatitis B core antigen (HBcAg) linked tandemly to a second recombinant HBcAg wherein (a) said first HBcAg and second HBcAg are joined directly or separated by an optional amino acid linker sequence, (b) one or both of said first HBcAg and said second HBcAg have a heterologous epitope in the e1 loop, (c) the tandemly linked said first HBcAg and second HBcAg form core particles, and (d) one or both of said first HBcAg and said second HBcAg are optionally truncated at the C-terminus with a truncation that does not go beyond amino acid residue 144.

19. The particle according to claim 18 wherein the protein is a dimer of two copies of HBcAg.

20. The particle according to claim 19 wherein one of said first HBcAg and said second HBcAg has a heterologous epitope in the e1 loop.

21. The particle according to claim 19 wherein both of said first HBcAg and said second HBcAg have a heterologous epitope in the e1 loop.

22. The particle according to claim 21 wherein both of said first HBcAg and said second HBcAg have the same heterologous epitope in the e1 loop.

23. The particle according to claim 21 wherein each of said first HBcAg and said second HBcAg has a different heterologous epitope in the e1 loop.

24. The particle according to claim 19 wherein one or both of the heterologous epitopes are from the pre-S1 or pre-S2 region of hepatitis B virus (HBV).

25. The particle according to claim 19 wherein one or both of the heterologous epitopes consist of an amino acid sequence that is 10 to 120 amino acids residues in length.

26. The particle according to claim 19 wherein one or both of said first HBcAg and said second HBcAg are truncated at the C-terminus.

27. The particle according to claim 19 wherein said first HBcAg and said second HBcAg are joined by a linker.

28. The particle according to claim 19 wherein the linker is at least 1.5 nm in length.

29. The particle according to claim 27 wherein the linker comprises multiple copies of the sequence GlyGlySer (GGS).

30. The particle according to claim 29 wherein the linker comprises 5, 6 or 7 copies of the sequence GGS.

31. A pharmaceutical composition comprising a fusion protein comprising a first recombinant hepatitis B core antigen (HBcAg) linked tandemly to a second recombinant HBcAg wherein (a) said first HBcAg and second HBcAg are joined directly or separated by an amino acid linker sequence, (b) one or both of said first HBcAg and said second HBcAg have a heterologous epitope in the e1 loop, (c) the tandemly linked said first HBcAg and second HBcAg form core particles, and (d) one or both of said first HBcAg and said second HBcAg are optionally truncated at the C-terminus with a truncation that does not go beyond amino acid residue 144 and a pharmaceutically acceptable carrier or diluent.

32. The pharmaceutical composition according to claim 31 wherein the protein is a dimer of two copies of HBcAg.

33. The pharmaceutical composition according to claim 32 wherein one of said first HBcAg and said second HBcAg has a heterologous epitope in the e1 loop.

34. The pharmaceutical composition to claim 32 wherein both of said first HBcAg and said second HBcAg have a heterologous epitope in the e1 loop.

35. The pharmaceutical composition according to claim 34 wherein both of said first HBcAg and said second HBcAg have the same heterologous epitope in the e1 loop.

36. The pharmaceutical composition according to claim 34 wherein each of said first HBcAg and said second HBcAg has a different heterologous epitope in the e1 loop.

* * * * *